United States Patent [19]

Thuillier born Nachmias et al.

[11] 4,017,632
[45] Apr. 12, 1977

[54] PHENOXYACETIC ACID DERIVATIVES

[75] Inventors: Germaine Thuillier born Nachmias, Paris; Jacqueline Suzanne Laforest born Boutillier du Retail, Vincennes; Bernard Jean Marie Cariou, Combleux; Pierre Alfred René Bessin, Chilly Mazarin; Jacqueline Suzanne Bonnet born Roux; Jean Eugène Thuillier, both of Paris, all of France

[73] Assignee: Centre Europeen de Recherches Pharmacologiques C.E.R.P.H.A., Arcueil, France

[22] Filed: Oct. 22, 1975

[21] Appl. No.: 624,648

[52] U.S. Cl. .............................. 424/275; 424/285; 260/332.2 A; 260/347.5

[51] Int. Cl.$^2$ ................ A61K 31/38; A61K 31/34

[58] Field of Search ................ 260/332.2 A, 347.3; 424/275, 285

[56] References Cited

UNITED STATES PATENTS

| | | | |
|---|---|---|---|
| 3,422,196 | 1/1969 | Thoma et al. ..................... | 424/285 |
| 3,758,506 | 9/1973 | Godfroid et al. ................. | 424/275 |

*Primary Examiner*—Frederick E. Waddell
*Attorney, Agent, or Firm*—Stevens, Davis, Miller & Mosher

[57] ABSTRACT

The present application relates to phenoxy-acetic derivatives, the preparation thereof and pharmaceutical compositions containing them.

7 Claims, No Drawings

PHENOXYACETIC ACID DERIVATIVES

BACKGROUND OF THE INVENTION

In recent years, various research efforts have been reported in the area of diuretic medicines.

In our U.S. Pat No. 3.758.506 phenoxy acetic acid derivatives which are 4-(2-furyl-keto), (2-thienyl-keto) and [2-(5-methyl)-thienyl-keto]-2,3-dichloro-phenoxyacetic acids, have been described.

DESCRIPTION OF THE INVENTION

According to the present invention there is provided a phenoxy-acetic acid derivative of the general formula

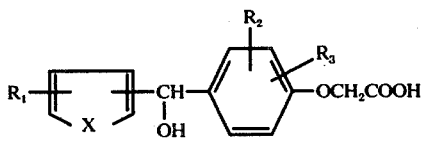

wherein X is oxygen or sulfur, and $R_1$, $R_2$ and $R_3$ which may be identical or different each represents a hydrogen atom, a halogen atom or a $C_{1-4}$ alkyl group.

The salts of the compounds (alkali metal salts and salts with pharmaceutically acceptable bases) are an object of the invention.

The compounds of the invention are prepared by reduction of the ketones having the formula

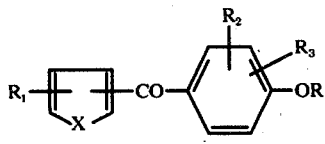

wherein X, $R_1$, $R_2$ and $R_3$ are defined as above and R is the group $CH_2COOH$ or a hydrogen atom, by an alkali borohydride such as sodium borohydride, in a basic medium, the preferred solvents being water, alcohol or dioxan.

When R is H, the reduction if followed by the reaction between the compound obtained after the reduction and an α-halogeno-acetic acid or ester in a basic medium for obtaining the compound of formula I.

If an α-halogeno-acetic ester is used, the intermediate ester is hydrolysed.

The salts of the acids of formula I are prepared by reacting an alkaline or organic base with the acid in solvents such as alcohols and ketones.

The following Examples will serve to illustrate the invention.

Example 1 :
2.3-dichloro-4-(2-thienyl-hydroxy-methyl)phenoxy-acetic acid a) α-(2-thienyl)-2.3-dichloro-4-hydroxy-benzyl alcohol A solution of 27.3 g of 2-thienyl (2.3-dichloro-4-hydroxy-phenyl) ketone in 250 ml of 0.2 N sodium hydroxide is poured into a solution of 2.9 g of sodium borohydride in 27 ml of 0.2 N sodium hydroxide. 20 hours after, the mixture is acidified with acetic acid and then hydrochloric acid (or phosphoric or sulfuric acid). The precipitate is crystallized from chloroform. 21 g of alcohol are obtained. Melting point = 146° C.

b) 2,3-dichloro-4-(2-thienyl-hydroxy-methyl)-phenoxy-acetic acid 10 g of phenol, 2.04 g of potassium hydroxide and 300 mg of potassium iodide are dissolved in 50 ml of ethanol. After 3 hours boiling, the precipitate is filtered and the solvent evaporated. The leftover oil is dissolved in ethylether, the organic phase washed with aqueous sodium hydroxide, with water and the solvent is evaporated. The oil is dissolved with 1 g of potassium hydroxide in aqueous ethanol (80%). After one hour boiling the ethanol is evaporated, the residue dissolved in water and the solution acidified. The precipitate is crystallized again from 1,2-dichloroethane and methylene chloride. 5 g of 2,3-dichloro-4-(2-thienyl-hydroxymethyl)-phenoxyacetic acid are obtained. Melting point = 163° C.

The salts of this acid are prepared by action of one equivalent of a base on the acid in solution in hot ethanol.

- sodium salt ($C_{13}H_9Cl_2O_4SNa$) melting point = 263° C
- piperazine addition salt ($C_{30}H_{20}Cl_4N_2O_8S_2$) melting point = 208° C

Example 2 :
2,3-dichloro-4-(2-furyl-hydroxy-methyl)-phenoxyacetic acid

According to the process described in example 1, the following products are obtained:

α-(2-furyl)-2,3-dichloro-4-hydroxy-benzyl alcohol, melting point = 137° C (from carbon tetrachloride).

Ethyl 2,3-dichloro-4-(2-furyl-hydroxy-methyl) phenoxy-acetate, melting point : 110° C (from diisopropyloxide).

2,3-dichloro-4-(2-furyl-hydroxy-methyl)-phenoxyacetic acid, melting point < 80° C (with decomposition).

Example 3 :
2,3-dichloro-4-[2-(5-chloro)-thienyl-hydroxymethyl]-phenoxy-acetic acid According to the process described in example 1, the following products are obtained:

α-[2-(5-chloro)thienyl]-2,3-dichloro-4-hydroxybenzyl alcohol, melting point = 139° C (from carbontetrachloride).

Ethyl 2,3-dichloro-4-[2-(5-chloro)-thienyl-hydroxymethyl]-phenoxy-acetate, melting point = 104° C (from cyclohexane/benzene).

2,3-dichloro-4-[2-(5-chloro)-thienyl-hydroxymethyl]phenoxy-acetic acid, melting point = 145° C (from 1,2-dichloro-ethane).

N-N-diethylamine addition salt ($C_{17}H_{20}Cl_3N\,S\,O_4$) melting point = 146° C.

Example 4 :
3-chloro-4-(2-thienyl-hydroxy-methyl)-phenoxy-acetic acid

According to the process described in example 1, the following products are obtained :

α-(2-thienyl)-3-chloro-4-hydroxy-benzyl alcohol, melting point : 130°C.

Ethyl 3-chloro-4-(2-thienyl-hydroxy-methyl)-phenoxy-acetate, melting point : 75°C.

3-chloro-4-(2-thienyl-hydroxy-methyl)-phenoxy-acetic acid, melting point : 95°C (with decomposition).

Example 5:
2,6-dibromo-4-(2-thienyl-hydroxy-methyl)-phenoxy-acetic acid

According to the process described in example 1, the following products are obtained:

α-(2-thienyl)-2,6-dibromo-4-hydroxy-benzyl alcohol, melting point: 175°C.

Ethyl 2,6-dibromo-4-(2-thienyl-hydroxy-methyl)-phenoxy-acetate, melting point: 85°C.

2,6-dibromo-4-(2-thienyl-hydroxy-methyl)-phenoxy-acetic acid, melting point: 156°C.

Example 6:
2,3-dimethyl-4(2-thienyl-hydroxy-methyl-phenoxy-acetic acid

A solution of 8.15 g (0.28 mole) of 2,3-dimethyl-4-(2-thienyl-keto)-phenoxy-acetic acid and 2.1 g of sodium hydroxide in 75 ml of water is poured into 10 ml of a 0.2 N sodium hydroxide aqueous solution containing 1 g of sodium borohydride. The mixture is stirred 24 hours, then acidified with acetic acid and hydrochloric acid. The precipitate is filtered and crystallized from a mixture of acetone and water. 6.5 g of 2,3-dimethyl-4-(2-thienyl-hydroxy-methyl)-phenoxy-acetic acid are obtained, melting point: 155°C.

Example 7:
4-(2-thienyl-hydroxy-methyl)-phenoxy-acetic acid

According to the process described in example 6, the product is obtained with nearly the same yield. The sodium salt which crystallizes with ethanol ($C_{15}H_{17}O_5S$ Na) melts at 192°C.

The compounds of the invention have diuretic and uricosuric activity as demonstrated in various pharmacological procedures. More specifically, the compound of example 1 prepared as noted above, has been tested in different pharmacological experiments summarized as follows.

Acute toxicity

The compounds were administered in the usual way to lots of 10 male mice (Swiss C.D) of average weight 20 g. Mortality was assessed after 48 hours for toxicity per os. The results are given in Table I.

| Compound | LD 50 per os mg/kg |
|---|---|
| example 1 | 1000 |
| example 5 | >1000 |
| benziodarone | 1400 |

Diuretic activity

The activity is determined on mice. The ratio R of the mean values of diuresis obtained for the treated animals to the mean values for control animals are determined.

For instance, for the compound of example 1 (dosis 100mg/kg P.O.) R is 1.6.

For ethacrynic acid (dosis 20 mg/kg P.O.) R = 2.4, the DL 50 P.O. being 600 mg/kg.

Uricosuric activity

This activity was determined by the ability of the compounds to cause retention of phenol red in the circulation of the rat, method described by
KREPPEL E. Med. Exptl. 1 285 (1959) and
SCARBOROUGH H. C. and M. C. KINNEY G. R. — J. Med. Pharm. Chem. 5 175 (1962)

The products were administered one hour before phenol red injection to batches of 5 rats of 250–280 g; anesthetized with ether, the animals received an I.V. injection of 1 cm3 of a 1% phenol red solution. Blood samplings were made 15, 30, 45 and 60 minutes after injection. The pink colour develop after addition to the plasma of an N/10 aqueous solution of sodium hydroxide.

For instance the compounds of examples 5 and 1, and benziodarone give the following results for a dosis of 100 mg/kg per os.

| | % of retention | | | |
|---|---|---|---|---|
| | 15 mn | 30 mn | 45 mn | 60 mn |
| Example 5 | 68 % | 123 % | 105 % | 58 % |
| Example 1 | 51 % | 44 % | 31 % | 28 % |
| Benziodarone | 37 % | 50 % | 53 % | 18 % |

The uricosuric activity of the compound of example 1 was further studied.

The uricosuric activity is determined by intravenous administration of a test compound to the phosphate-mannitol infused mongrel dog as a rapid injection at doses of 5 or 15 mg/kg. Renal clearance studies are compared against control experiments conducted in the same dogs. The urate clearance is calculated from the plasma and urinary concentrations. In this study, compound of example 1 markedly increased the urinary excretion and clearance of uric acid. For example, compound of example 1 at a dose of 5 mg/kg i.v. increased urate excretion as a percentage of glomerular filtration rate from a value of 27% up to 40% and at a dose of 15 mg/kg i.v. increased it from 28% up to 74%.

The compounds of the invention and their salts are useable in human and veterinary therapy as diuretics, hypotensives and uricosurics.

These compounds can be used as active principles associated or not with other appropriate active principles, in the principal pharmaceutically suitable forms, such as tablets, capsules, suppositories and injectable solutions.

For per os administration, for suppositories, and for injectable solutions the dose can be from 0.01 g. to 1 g of active product.

The compounds can be administered in daily doses varying from 100 to 1500 mg at these doses, they do not provoke any undesirable secondary phenomena; in particular, potassium loss is relatively weak.

An example of typical formulation is as follows:

| FORMULATION 1. - FOR TABLETS | |
|---|---|
| | G |
| Active principle | 0.500 |
| Potato starch | 0.020 |
| Polyvinyl pyrrolidone | 0.020 |
| Maize starch | 0.045 |
| Talc | 0.020 |
| Magnesium stearate | 0.015 |

We claim:

1. A phenoxyacetic acid derivative selected from the group consisting of a phenoxyacetic acid of the general formula

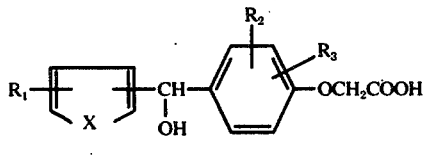

wherein X is oxygen or sulfur and $R_1$, $R_2$ and $R_3$ which may be identical or different, each represents a hydrogen atom, a halogen atom or a $C_{1-4}$ alkyl group, an alkali metal salt thereof and an additional salt thereof with a pharmaceutically acceptable base.

2. A compound selected from the group consisting of 2.3-dichloro:4-[(2-thienyl)-hydroxy-methyl]-phenoxyacetic acid, an alkali metal salt thereof and an additional salt thereof with a pharmaceutically acceptable base.

3. A compound selected from the group consisting of 2,6-dibromo-4-[(2-thienyl)-hydroxy-methyl]-phenoxyacetic acid, an alkali metal salt thereof and an additional salt thereof with a pharmaceutically acceptable base.

4. A therapeutic composition adapted to be used as a diuretic which contains as active principle a daily dosage of from about 100 to about 1500 mg. of at least one phenoxyacetic acid compound selected from the group consisting of a phenoxyacetic acid of the general formula:

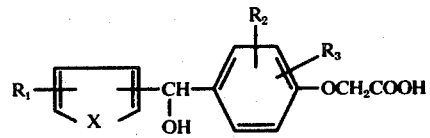

wherein X is oxygen or sulfur and $R_1$, $R_2$ and $R_3$ which may be identical or different, each represents a hydrogen atom, a halogen atom or a $C_{1-4}$ alkyl group, an alkali metal salt thereof and an additional salt thereof with a pharmaceutically acceptable base.

5. The composition of claim 4 as a suppository containing from 0.01g to 1g of active product.

6. The composition of claim 4 as an injectable solution containing from 0.01g to 1g of active principle.

7. The method of treating a human or animal with a diuretic which comprises administering thereto the composition of claim 4.

* * * * *